United States Patent [19]

Izzo et al.

[11] Patent Number: 5,560,955

[45] Date of Patent: *Oct. 1, 1996

[54] PROTEIN COMPOSITIONS HAVING REDUCED-HYDROSCOPIC PROPERTIES AND METHODS FOR PREPARING SAME

[75] Inventors: Henry J. Izzo, Bridgewater; Robert E. Lieberman, Morris Township, both of N.J.

[73] Assignee: Healthy Foods Solutions, Morris Township, Morris County, N.J.

[ * ] Notice: The term of this patent shall not extend beyond the expiration date of Pat. No. 5,240,734.

[21] Appl. No.: 327,486

[22] Filed: Oct. 21, 1994

Related U.S. Application Data

[63] Continuation-in-part of Ser. No. 708,484, May 31, 1991, Pat. No. 5,240,734.

[51] Int. Cl.$^6$ ............................................. A23L 1/38
[52] U.S. Cl. ...................... 426/633; 426/44; 426/631; 426/654; 426/656; 426/657
[58] Field of Search ........................... 426/633, 654, 426/631, 656, 657, 44

[56] References Cited

U.S. PATENT DOCUMENTS

| | | | |
|---|---|---|---|
| 2,147,549 | 2/1939 | Roselius | 426/631 |
| 5,240,734 | 8/1993 | Izzo et al. | 426/633 |
| 5,273,773 | 12/1993 | Katayama et al. | 426/656 |

*Primary Examiner*—Helen Pratt
*Attorney, Agent, or Firm*—Richard Muccino

[57] ABSTRACT

This invention pertains to protein compositions having reduced-hygroscopic properties which comprise a homogeneous premixture of (a) a hygroscopic protein and (b) an effective amount of a protein complexing agent to reduce the hygroscopic properties of the protein. The reduced-hygroscopic protein compositions may be used directly or may be incorporated in effective amounts into edible carriers to provide a wide variety of edible compositions. This invention also pertains to methods for preparing these improved protein compositions and the edible compositions in which they may be employed.

21 Claims, No Drawings

5,560,955

PROTEIN COMPOSITIONS HAVING REDUCED-HYDROSCOPIC PROPERTIES AND METHODS FOR PREPARING SAME

This application is a continuation-in-part of U.S. application Ser. No. 708,484 filed on 31 May 1991 now U.S. Pat. No. 5,240,734.

BACKGROUND OF THE INVENTION

1. Field of the Invention

This invention pertains to protein compositions having reduced-hygroscopic properties. More particularly, this invention pertains to reduced-hygroscopic protein compositions which comprise a homogeneous premixture of a hygroscopic protein and an effective amount of a protein complexing agent to reduce the hygroscopic properties of the protein. The improved protein compositions may be used directly or may be incorporated into edible carriers to provide a wide variety of edible compositions.

2. Description of the Background

Foods such as peanut butter, pasta, and rice serve as important sources of protein. Because these foods contain proteins which are hygroscopic, the processing and extruding of these foods are often difficult. Mixtures of these protein sources with other foods containing water tend to become thick, dry, and stiff. Extruding these foods generally requires large amounts of water to soften these materials making processing difficult and expensive. Accordingly, methods for reducing the hygroscopic properties of proteins in foods to facilitate handling are highly desirable.

A particularly rich source of protein is peanut butter which has a protein content in the range from about 23% to about 26%. The oil or fat content of peanut butter, however, is in the range from about 48% to about 53% mitigating the nutritional value of peanut butter. Attempts to make low-fat peanut butter have generally focused on removing a portion of the peanut oil found in peanuts and replacing the oil with a low-fat and low-calorie filler substitute. These low-calorie peanut butter compositions have generally been unsatisfactory because the peanut oil removal step tends to also remove a portion of the flavor components from the peanut butter resulting in a peanut butter with poor taste. In addition, the low-fat filler substitutes generally do not provide the texture and consistency properties of conventional peanut butter. Aqueous low-fat filler substitutes, in particular, tend to be absorbed by the hygroscopic peanut butter protein resulting in dry, undesirable, peanut butter compositions. Accordingly, low-fat peanut butters having reduced-hygroscopic properties but with the flavor and texture of conventional peanut butters are desirable.

U.S. Pat. No. 4,863,753, issued to Hunter et al., discloses a reduced-calorie peanut butter composition in which a portion of the peanut oil is replaced by triglycerides containing medium chain fatty acids.

U.S. Pat. No. 4,814,195, issued to Yokoyama et al., discloses a reduced-calorie peanut butter composition containing from about 15% to about 40% of a low-calorie solid bulking agent such as polydextrose or microcrystalline cellulose.

U.S. Pat. No. 4,228,190, issued to Wallgren et al., discloses a margarine composition in the form of a water-in-oil emulsion which comprises a fat phase present in an amount from about 35% to about 65% and an aqueous precipitated protein phase, present in an amount from about 35% to about 65%. Wallgren et al. forms the aqueous precipitated protein phase by coagulating milk protein with rennet and the calcium already present in casein. Wallgren et al. does not teach to add a protein complexing agent.

U.S. Pat. No. 3,580,729, issued to Darragh et al., discloses a peanut spread supplemented with from about 15% to about 25% of soybean protein and from about 15% to about 25% of liquid vegetable oil.

U.S. Pat. No. 3,552,980, issued to Cooper et al., discloses a spreadable food product consisting of two discrete spreads in contact with each other. One spread is hydrophilic such as a peanut butter and the other spread is a modified sweet aqueous spread such as a jelly. The sweet aqueous spread is modified to contain in the non-aqueous portion less than 50% carbohydrates having a molecular weight of less than about 200 to prevent migration of moisture from the sweet aqueous spread to the hydrophilic spread.

U.S. Pat. No. 2,388,991, issued to Oatman, discloses a method for precipitating casein from dried skim milk which consists of mixing the dried skim milk with fresh skim milk and precipitating the casein with an acid, sour whey, or rennet.

While the above references disclose a variety of improved food compositions, none of the above disclosures has solved the difficulty in processing hygroscopic proteins. Thus it would be commercially advantageous to provide protein compositions having reduced-hygroscopic properties to facilitate the processing of these foods. The present invention provides such improved protein compositions having reduced-hygroscopic properties without the disadvantages characteristic of previously known products. This invention also pertains to methods for preparing these reduced-hygroscopic protein compositions and the edible compositions in which they may be employed.

SUMMARY OF THE INVENTION

This invention pertains to protein compositions having reduced-hygroscopic properties which comprise a homogeneous premixture of (a) a hygroscopic protein and (b) an effective amount of a protein complexing agent to reduce the hygroscopic properties of the protein. The reduced-hygroscopic protein compositions may be used directly or may be incorporated in effective amounts into edible carriers to provide a wide variety of edible compositions. This invention also pertains to methods for preparing these improved protein compositions and the edible compositions in which they may be employed.

In a preferred embodiment, the invention pertains to a reduced-fat peanut butter composition in the form of a water-in-oil emulsion which comprises:

(A) a premixed continuous peanut butter oil phase which comprises:
  (a) peanut butter; and
  (b) an effective amount of a protein complexing agent to reduce the hygroscopic properties of the peanut butter; and (B) a discontinuous coagulated protein aqueous phase to reduce the fat content of the peanut butter composition present in an amount from about 10% to about 90%, by weight, which comprises:
  (a) a coagulable protein selected from the group of dairy and vegetable proteins consisting of milk protein, egg protein, soy bean protein, and peanut protein present in the discontinuous coagulated protein aqueous phase in an amount from about 1% to about 30%, by weight; and
  (b) a protein coagulating agent.

DETAILED DESCRIPTION OF THE INVENTION

Applicants have found that when conventional protein compositions are treated with water, the hygroscopic properties of the proteins cause the compositions to become thick, dry, lumpy, and difficult to process. Moreover, the shearing necessary to blend or knead the mixture frequently generates heat further complicating handling and jeopardizing the stability of the mixture. Applicants have discovered that the hygroscopic properties of protein compositions can be reduced by premixing the protein with a protein complexing agent. Protein compositions premixed with a protein complexing agent according to the present invention retain a smooth consistency when treated with water, do not become lumpy, and are easier to handle. The reduced-hygroscopic protein compositions also require less water to process and are easier to extrude. Applicants believe that when a protein complexing agent is premixed with a hygroscopic protein, the protein complexes with the complexing agent causing a change in conformation of the protein which results in a decrease in hygroscopicity. This reduced hygroscopicity results in protein compositions that have improved consistency, are easier to extrude, and are easier to mix with other foods.

In a preferred embodiment, the reduced-hygroscopic protein compositions are reduced-fat peanut butter compositions in the form of water-in-oil emulsions. The emulsion comprises a continuous peanut butter oil phase and a discontinuous coagulated protein aqueous phase. The continuous oil phase comprises peanut butter and an effective amount of a protein complexing agent to reduce the hygroscopic properties of the protein. The discontinuous aqueous phase comprises a coagulable protein and a protein coagulating agent. Complexing the peanut butter protein in the oil phase with a complexing agent reduces the hygroscopic properties of the protein and permits the oil phase to be smoothly mixed with the aqueous phase. Coagulating the protein in the discontinuous aqueous phase physically stabilizes the aqueous phase and maintains the consistency of conventional peanut butter. The coagulated protein aqueous phase acts as a nutritious extender to reduce the fat content of the peanut butter. Additional non-coagulable protein may also be added to the aqueous phase to enhance the protein content of the peanut butter. By carefully controlling the temperature and time of the protein coagulation and the concentration of the protein complexing agent, the peanut butter oil phase and the aqueous protein phase can be smoothly mixed without causing separation of the peanut oil and peanut particle phases. Because the continuous oil phase contains peanut butter in undiluted form, the taste and consistency of the reduced-fat peanut butter composition is substantially the same as that of conventional peanut butter flavor.

Applicants define the terms "ingestible" and "edible" to include all materials and compositions which are used by or which perform a function in the body. These include materials and compositions which are adsorbed and those which are not absorbed as well as those which are digestible and non-digestible.

In accord with the present invention, a protein composition having reduced-hygroscopic properties may be prepared by premixing a hygroscopic protein and an effective amount of a protein complexing agent to reduce the hygroscopic properties of the protein. The hygroscopic proteins which may be employed in the present invention may be any edible hygroscopic protein. Non-limiting examples of hygroscopic proteins may be selected from the group consisting of dairy, vegetable, and meat proteins.

Examples of dairy protein include milk and egg protein. The term "milk protein" as used herein refers to proteins present or derived from milk. Milk proteins include proteins derived from whole milk, low-fat milk, non-fat milk, buttermilk, powdered milk, and the like. The main proteins found in milk are casein, present in an amount of about 80%, and whey proteins which are beta-lactoglobulin or lactalbumin, present in an amount of about 20%.

The term "egg protein" as used herein is used in its common meaning and refers to proteins present or derived from egg. Egg proteins include proteins derived from egg white, dried egg white, and the like. The main protein found in egg is ovalbumin (egg white).

Examples of vegetable protein include soy bean, wheat (such as semolina), corn, rice, oat, peanut, and legume protein. The term "vegetable protein" as used herein is used in its common meaning and refers to proteins present or derived from the vegetable, meal, oil meal, flour, and the like. The term "legume" refers to the pod or fruit of a leguminous plant, such as peas or beans. A preferred vegetable protein is semolina.

The term "peanut protein" as used herein is used in its common meaning and refers to proteins present or derived from peanuts, peanut meats, peanut oil meal, and the like. Peanuts contain about 26% protein and peanut oil meal contains from about 39% to about 45% protein. The main proteins found in peanuts are the globulins, arachin, and conarachin.

Examples of meat protein include bovine, porcine, and lamb protein. The term "meat protein" as used herein is used in its common meaning and refers to proteins present or derived from animal meats.

The protein complexing agent in the present invention is a compound which will complex with the hygroscopic protein, reduce the hygroscopicity of the protein, and enhance mixing of the protein. Preferably, the protein complexing agent is a divalent metal ion selected from the group consisting of non-toxic water-soluble calcium compounds and magnesium compounds. Suitable non-limiting examples of calcium and magnesium compounds include calcium chloride, calcium carbonate, calcium sulfate, calcium lactate, calcium oxalate, calcium gluconate, calcium propionate, magnesium chloride, magnesium carbonate, magnesium sulfate, magnesium lactate, magnesium oxalate, magnesium gluconate, magnesium propionate, and the like, and mixtures thereof. In a preferred embodiment, the protein complexing agent is a calcium compound selected from the group consisting of calcium gluconate, calcium lactate, calcium propionate, and mixtures thereof. In a more preferred embodiment, the calcium compound is calcium gluconate.

The amount of protein complexing agent present in the reduced-hygroscopic protein compositions of the present invention is an effective amount. An effective amount of protein complexing agent is that amount of protein complexing agent necessary to reduce the hygroscopic properties of the protein. The exact amount of protein complexing agent employed is subject to such factors as the type of hygroscopic protein and protein complexing agent employed in the mixture, the other ingredients in the composition, and the type of final product desired. The exact amount of protein complexing agent employed may be varied in order to obtain the result desired in the final product and such variations are within the capabilities of those skilled in the art without the need for undue experimentation. In a preferred embodiment, the protein complexing agent will be present in the reduced-hygroscopic protein composition in an amount from about 0.1% to about 13%, preferably from about 0.2% to about 8.5%, and more preferably from about 0.3% to about 7%, by weight.

The present invention extends to methods for making the protein compositions having reduced-hygroscopic properties. In a typical method, the reduced-hygroscopic protein compositions are prepared by admixing the hygroscopic protein and the protein complexing agent. The components may be admixed using standard techniques and apparatus known to those skilled in the art. Other ingredients will usually be incorporated into the composition as dictated by the nature of the desired composition as well known by those having ordinary skill in the art. The ultimate protein compositions are readily prepared using methods generally known in the food technology and confectionery arts.

Once prepared, the reduced-hygroscopic protein compositions may be used directly, may be stored for future use, or may be formulated in effective amounts with conventional edible carriers to prepare a wide variety of edible compositions such as cookies, candies, chocolates, butters, jellies, jams, sauces, and the like.

The preparation of edible and confectionery formulations is historically well known and has changed little through the years. The reduced-hygroscopic protein compositions of the present invention can be incorporated into edible carriers by admixing the inventive reduced-hygroscopic protein compositions into conventional confections.

Suitable edible carriers and confectionery bulking agents in the present invention include sweetening agents selected from the group consisting of, but not limited to, monosaccharides, disaccharides, polysaccharides, sugar alcohols, and mixtures thereof; randomly bonded glucose polymers such as those polymers distributed under the tradename POLYDEXTROSE by Pfizer, Inc., Groton, Conn.; isomalt (a racemic mixture of alpha-D-glucopyranosyl-1,6-mannitol and alpha-D-glucopyranosyl- 1,6-sorbitol manufactured under the tradename PALATINIT by Suddeutsche Zucker), maltodextrins; hydrogenated starch hydrolysates; hydrogenated hexoses; hydrogenated disaccharides; minerals, such as calcium carbonate, talc, titanium dioxide, dicalcium phosphate, celluloses, and the like, and mixtures thereof.

Suitable sugar bulking agents include monosaccharides, disaccharides and polysaccharides such as xylose, ribulose, glucose (dextrose), mannose, galactose, fructose (levulose), sucrose (sugar), maltose, invert sugar, partially hydrolyzed starch and corn syrup solids, and mixtures thereof. A preferred suitable sugar bulking agent is Di-Pac which is a co-crystallization mixture of 97% sucrose and 3% highly modified dextrines. Di-Pac and mixtures of sucrose and corn syrup solids are the more preferred sugar bulking agents.

Suitable sugar alcohol bulking agents include sorbitol, xylitol, mannitol, galactitol, maltitol, and mixtures thereof. Mixtures of sorbitol and mannitol are the preferred sugar alcohol bulking agents.

Maltitol is a sweet, water-soluble sugar alcohol useful as a bulking agent in the preparation of beverages and foodstuffs and is more fully described in U.S. Pat. No. 3,708,396, which disclosure is incorporated herein by reference. Maltitol is made by hydrogenation of maltose which is the most common reducing disaccharide and is found in starch and other natural products.

Suitable hydrogenated starch hydrolysates include those disclosed in U.S. Pat. Nos. Re. 25,959, 3,356,811, 4,279,931 and various hydrogenated glucose syrups and/or powders which contain sorbitol, hydrogenated disaccharides, hydrogenated higher polysaccharides, or mixtures thereof. Hydrogenated starch hydrolysates are primarily prepared by the controlled catalytic hydrogenation of corn syrups. The resulting hydrogenated starch hydrolysates are mixtures of monomeric, dimeric, and polymeric saccharides. The ratios of these different saccharides give different hydrogenated starch hydrolysates different properties. Mixtures of hydrogenated starch hydrolysates, such as LYCASIN, a commercially available product manufactured by Roquette Freres of France, and HYSTAR, a commercially available product manufactured by Lonza, Inc., of Fairlawn, N.J., are also useful.

A variety of traditional ingredients may be optionally included in effective amounts in the edible composition. Such ingredients include antioxidants, preservatives, and the like. Suitable anti-oxidants include butylated hydroxytoluene (BHT), butylated hydroxyanisole (BHA), propyl gallate, and mixtures thereof. Suitable preservatives include potassium sorbate, sodium benzoate, calcium propionate, and mixtures thereof. Other conventional additives known to one having ordinary skill in the food and confectionery art may also be used in the edible composition.

A general discussion of the composition and preparation of confections may be found in B. W. Minifie, *Chocolate, Cocoa and Confectionery:* Science and Technology, 2nd edition, AVI Publishing Co., Inc., Westport, Conn. (1980), at pages 424–425, which disclosure is incorporated herein by reference.

The amount of the inventive reduced-hygroscopic protein compositions employed in an edible composition is an effective amount to provide satisfactory flavor and nutritional value to the edible composition. The exact amount of the reduced-hygroscopic protein compositions employed is a matter of preference, subject to such factors as the type of edible carrier employed in the composition, the type of reduced-hygroscopic protein composition employed, and the other ingredients in the composition. Thus, the amount of reduced-hygroscopic protein composition may be varied in order to obtain the result desired in the final product and such variations are within the capabilities of those skilled in the art without the need for undue experimentation. In general, the amount of reduced-hygroscopic protein composition normally present in an edible composition will be up to about 90%, preferably from about 20% to about 85%, and more preferably from about 25% to about 80%, by weight of the edible composition.

The present invention extends to methods for making the edible compositions. In such a method, an edible composition is made by first premixing a hygroscopic protein and a protein complexing agent to form a reduced-hygroscopic protein composition of the present invention. An effective amount of the reduced-hygroscopic protein composition is then admixed with an edible carrier and the other ingredients of the final desired edible composition. The reduced-hygroscopic protein composition may be admixed with the edible carrier in any conventional manner such as by preparing a homogeneous mixture of the components, forming a protein composition core coated by an edible carrier such as chocolate, or coating a confectionery carrier with the protein composition. Other ingredients will usually be incorporated into the composition as dictated by the nature of the desired composition as well known by those having ordinary skill in the art. The ultimate edible compositions are readily prepared using methods and apparatus generally known in the food technology arts.

In a particularly preferred embodiment, the reduced-hygroscopic protein composition is a reduced-fat peanut butter composition in the form of a water-in-oil emulsion. The emulsion comprises a continuous peanut butter oil phase and a discontinuous coagulated protein aqueous phase. The continuous oil phase comprises peanut butter and an effective amount of a protein complexing agent to reduce the hygroscopic properties of the protein. The discontinuous aqueous phase comprises a coagulable protein and a protein coagulating agent.

The peanut butter which may be employed in the continuous oil phase may be any peanut butter known in the art. In general, peanut butter comprises peanut paste, a stabilizing agent, and optionally an emulsifying agent, a sweetening agent, and salt. Normally, peanut butter comprises peanut paste in an amount from about 75% to about 99% by weight of the peanut butter.

Peanut paste is obtained by roasting, blanching, and grinding raw peanuts by methods well known in the food arts. Peanut paste may be made from a variety of peanuts and is preferably prepared from a blend of Runner, Spanish, and Virginia peanuts. The peanuts may be ground in any conventional manner such as in a comminuter, an attrition mill, a disintegrator, a hammermill, or a colloid mill. The extent of grinding may be adjusted to prepare the desired type of peanut butter having a smooth, regular, or chunky texture. The resulting peanut paste is a mixture of peanut particles suspended in peanut oil.

A stabilizing agent is generally added to the peanut butter to stabilize the peanut butter against separation of the peanut oil and solid peanut components. The stabilizing agent is usually mixed with the peanut paste and heated to melt the stabilizing agent. The mixture is then cooled to solidify the stabilizing agent as a continuous or semicontinuous matrix to provide rigidity to and prevent phase separation of the peanut butter mixture. Stabilizing agents are well known in the art and include partially and completely hydrogenated vegetable oils, monoglycerides and diglycerides of vegetable oils, and mixtures of these. Non-limiting examples of stabilizing agents include partially and completely hydrogenated natural fats such as peanut oil, corn oil, cotton seed oil, linseed oil, palm oil, rapeseed oil having an iodine value not greater than about 10, whale oil, and other marine oils, and the like, and mixtures thereof. The stabilizing agent is generally present in the peanut butter in an amount from about 1% to about 5%, preferably from about 1.5% to about 3%, and more preferably from about 15% to about 2.5% by weight of the peanut butter oil phase.

An emulsifying agent may optionally be present in the peanut butter to aid in dispersing the immiscible components into a single stable system and to reduce stickiness so that the peanut butter will not adhere to the roof of the mouth. Non-limiting examples of emulsifying agents include glyceryl monostearate, lecithin, fatty acid monoglycerides, fatty acid diglycerides, propylene glycol monostearate, and the like, and mixtures thereof. A preferred emulsifying agent is glyceryl monostearate. The emulsifying agent may be employed in amounts from about 0.5% to about 1.5%, preferably from about 0.75% to about 1.25%, and more preferably from about 0.8% to about 1%, by weight of the peanut butter oil phase.

A sweetening agent may optionally be present in the peanut butter. Non-limiting examples of sweetening agents may be selected from the group consisting of sucrose, dextrose, fructose, honey, molasses, aspartame, saccharin, and the like, and mixtures thereof. The sweetening agent will be present in the peanut butter in an amount from about 1% to about 10%, preferably from about 1% to about 5%, and more preferably from about 1% to about 3%, by weight of the peanut butter oil phase.

The peanut butter may also optionally contain salt as a flavoring agent in an amount from about 1% to about 1.5%, by weight of the peanut butter oil phase.

In general, the peanut butter in the peanut butter oil phase is prepared by admixing peanut paste, the stabilizing agent, and optional peanut butter ingredients to provide a uniform mixture. The mixture is usually heated and then cooled to recrystallize the stabilizing agent as a matrix to prevent phase separation of the peanut butter mixture. Preferably, the peanut butter is prepared under an inert atmosphere such as a nitrogen atmosphere.

The protein complexing agent present with the peanut butter in the continuous oil phase is a compound which will complex with the peanut protein, reduce the hygroscopicity of the protein, enhance mixing of the peanut butter oil phase and the aqueous protein phase, and produce a smooth peanut butter consistency. Examples of protein complexing agents and the amounts to be employed have been set out above.

The discontinuous coagulated protein aqueous phase comprises an aqueous solution of a coagulable protein selected from the group of dairy and vegetable proteins consisting of milk protein, egg protein, soy bean protein, and peanut protein and a protein coagulating agent.

The coagulable protein in the discontinuous aqueous phase may be any edible protein which may be coagulated. Coagulation is the solidification of a solution into a gelatinous mass or an alteration of a disperse phase or of a dissolved solid which causes the separation of the system into a liquid phase and an insoluble mass known as a clot or curd. Non-limiting coagulable proteins may be selected from the group of dairy and vegetable proteins consisting of milk protein, egg protein, soy bean protein, and peanut protein.

The term "milk protein" as used herein refers to proteins present or derived from milk. Milk proteins include proteins derived from whole milk, low-fat milk, non-fat milk, buttermilk, powdered milk, and the like. The main proteins found in milk are casein, present in an amount of about 80%, and whey proteins which are beta-lactoglobulin or lactalbumin, present in an amount of about 20%.

Casein is a white, tasteless, odorless, nontoxic amorphous solid present to the extent of about 3% in bovine milk. Casein is a mixture of related phosphoproteins which contains all of the common amino acids and is rich in the essential amino acids. Casein is obtained from milk by removing the cream and acidifying the skimmed milk to cause casein to precipitate. Casein is also precipitated by lactic acid during fermentation of skimmed milk in cheese manufacture. The major components of casein are designated as alpha-, beta, gamma, and K-caseins, in order of decreasing electrophoresis mobility at pH 7.

Whey is the supernatant fluid remaining after precipitation of casein. The principle protein of bovine whey is beta-lactoglobulin, also known as lactalbumin, which constitutes from about 50% to about 60% of the whey protein.

The term "egg protein" as used herein is used in its common meaning and refers to proteins present or derived from egg. Egg proteins include proteins derived from egg white, dried egg white, and the like. The main protein found in egg is ovalbumin (egg white).

The term "soy protein" as used herein is used in its common meaning and refers to proteins present or derived from soy bean, soy bean meal, and the like. The main protein found in soy bean is grain and soybean albumins.

The term "peanut protein" as used herein is used in its common meaning and refers to proteins present or derived from peanuts, peanut meats, peanut oil meal, and the like. Peanuts contain about 26% protein and peanut oil meal contains from about 39% to about 45% protein. The main proteins found in peanuts are the globulins arachin and conarachin.

The term "albumin" refers to a group of simple naturally occurring proteins characterized by heat coagubility and solubility in dilute solution. The most common albumins are lactalbumin (milk), ovalbumin (egg white), serum albumin (blood serum), and grain and soybean albumins. As set out above, the coagulable protein may be selected from the group of dairy and vegetable proteins consisting of milk protein, egg protein, soy bean protein, and peanut protein, preferably from the group of dairy protein consisting of milk protein and egg protein, and most preferably the coagulable protein is milk protein. The most preferred milk protein is casein.

The amount of coagulable protein present in the discontinuous aqueous phase of the present invention is an effective amount. An effective amount of coagulable protein is that amount of coagulable protein necessary to physically stabilize the aqueous phase and maintain the consistency of a conventional peanut butter. The exact amount of coagulable protein employed is subject to such factors as the type of coagulable protein employed in the mixture, the type of peanut butter oil phase employed, the other ingredients in the composition, and the type of final product desired. The exact amount of coagulable protein employed in the discontinuous aqueous phase may be varied in order to obtain the result desired in the final product and such variations are within the capabilities of those skilled in the art without the need for undue experimentation. In a preferred embodiment, the coagulable protein in the discontinuous aqueous phase will be present in an amount from about 1% to about 30%, preferably from about 1.5% to about 25%, and more preferably from about 2% to about 20%, by weight of the discontinuous aqueous phase.

The protein coagulating agent in the present invention is an agent such as a proteolytic enzyme, an acid, or sour whey which will coagulate or clot the coagulable proteins of the invention. Suitable protein coagulating acids include lactic acid, hydrochloric acid, and sulfuric acid. The amount of protein coagulating acid present in the discontinuous aqueous phase of the present invention is an amount effective to coagulate the protein. Such amounts of coagulating acid are well known in the art and are not the subject of the present invention. In a preferred embodiment, the protein coagulating agent is a protein coagulating enzyme.

The protein coagulating enzymes in the present invention are proteolytic enzymes which will coagulate or clot the coagulable proteins of the invention. The protein coagulating enzyme is an enzyme which does not continue its hydrolytic activity after curd formation. In general, such enzymes are catalyzed by calcium which is normally present in the coagulable protein. Suitable protein coagulating enzyme may be selected from the group consisting of rennin, *Mucor miehei, Mucor pusillus, Endothia parasitica, porcine pepsin,* and mixtures thereof. Other proteolytic enzymes can be used to coagulate proteins providing that their hydrolytic activity does not continue after curd formation. In a preferred embodiment, the protein coagulating enzyme is selected from the group consisting of rennin and *Mucor miehei.*

Rennin (chymosin, rennase) is an endopeptidase secreted by the stomach which causes the curdling of milk. Rennin is a single polypeptide chain with internal disulfide bridges and has the power to coagulate 25,000 times its weight of milk. Rennet is a commercially available dried extract containing rennin which is used in the manufacture of cheese, rennet casein, junket and rennet custards.

The amount of protein coagulating enzyme present in the discontinuous aqueous phase of the present invention is an effective amount. An effective amount of protein coagulating enzyme is that amount of enzyme necessary to coagulate the coagulable protein in a suitable period of time. In general, the protein coagulating enzyme should coagulate the protein just after mixing of the peanut butter oil phase and the aqueous protein phase is complete and before the discontinuous aqueous phase becomes unstable. The protein coagulating enzyme should not coagulate the protein before mixing of the peanut butter oil phase and the aqueous protein phase is complete. When the protein is coagulated before mixing of the phases is complete, mixing becomes difficult and the heat generated during mixing can cause the phases to separate. The exact amount of protein coagulating enzyme employed is subject to such factors as the type of protein coagulating enzyme employed in the mixture, the type of coagulable protein employed, the temperature at which the mixing of the peanut butter oil phase and the aqueous protein phase is conducted, the other ingredients in the composition, and the type of final product desired. The exact amount of protein coagulating enzyme employed in the discontinuous aqueous phase may be varied in order to obtain the result desired in the final product and such variations are within the capabilities of those skilled in the art without the need for undue experimentation. In a preferred embodiment, the protein coagulating enzyme in the discontinuous aqueous phase will be present in an amount from about 0.01% to about 1.2%, preferably from about 0.01% to about 0.1%, and more preferably from about 0.01% to about 0.08%, by weight of the discontinuous aqueous phase.

The pH value of the aqueous phase is generally adjusted to optimize coagulation of the protein by the protein coagulating enzyme and to maximize the shelf stability of the reduced-fat peanut butter composition. In general, the pH of the discontinuous aqueous phase will be in the range from about 3.8 to about 6.5, preferably from about 4 to about 6, and more preferably from about 4.2 to about 5.8. The pH of the discontinuous aqueous phase can be adjusted by adding a pH adjusting or buffering agent such as sodium hexametaphosphate (sodium polymetaphosphate), citric acid, phosphoric acid, lactic acid, and mixtures thereof. The exact amount of pH adjusting or buffering agent necessary to obtain a particular pH value is well known and within the capabilities of those skilled in the art without the need for undue experimentation.

In another embodiment, the shelf stability of the reduced-fat peanut butter composition can be enhanced by incorporating water-soluble solids such as carbohydrates into the aqueous protein phase. Preferably, the water-soluble solids are added after the emulsion is formed, that is after the aqueous protein phase, containing the coagulable protein and the protein coagulating agent, is admixed with the peanut butter oil phase to minimize inhibition of the coagulation step. Non-limiting examples of water-soluble solids include dextrose, sucrose, fructose, maltodextrins such as low DE (dextrose equivalence) maltodextrins, lactose, vegetable gums such as acacias, guar, karaya, polydextrose, microcrystalline cellulose, and mixtures thereof. Preferred sources of sugar water-soluble solids are sugar syrups and light corn syrup. Preferred sources of reduced-calorie water-soluble solids are polydextrose and microcrystalline cellulose. Sufficient water-soluble solids should be incorporated into the aqueous protein phase to obtain a water activity in the range from about 0.6 to about 0.9, preferably from about 0.65 to about 0.85, and more preferably from about 0.68 to about 0.82. The soluble solids value will be in the range from about 55% to about 82%, preferably from about 60% to about 75%, by weight of the aqueous phase. Polydextrose may be employed as a plasticizing agent to promote fluidity in the emulsion and may be present in the range from about 1% to about 15%, preferably from about 1% to about 10%, and more preferably from about 1% to about 6%, by weight of the aqueous phase. The shelf stability of the reduced-fat peanut butter composition can also be improved by incorporating preservatives such as potassium sorbate and sodium benzoate into the composition and by pasteurizing the peanut butter composition.

In yet another embodiment, the texture and consistency of the reduced-fat peanut butter compositions can be enhanced by incorporating chelating agents into the aqueous high soluble solids phase prior to admixing the aqueous high soluble solids phase with the peanut butter oil phase. Peanut butter compositions which contain an aqueous high soluble solids phase tend to have a stringy texture because of the presence of metal ions. When a chelating agent is added to the aqueous high soluble solids phase, the chelating agent tends to chelate the metal ion, reduce the body of the aqueous composition, and prevent the formation of a stringy texture. Suitable chelating agents in the present invention include sodium hexametaphosphate, sodium acid pyrophosphate, sodium tripolyphosphate, sodium citrate, and the like, and mixtures thereof. In a preferred embodiment, the chelating agent is selected from the group consisting of sodium hexametaphosphate and sodium acid pyrophosphate, and mixtures thereof. In a more preferred embodiment, the chelating agent is sodium hexametaphosphate.

The amount of chelating agent present in the discontinuous aqueous phase of the present invention is an effective amount. An effective amount of chelating agent is that amount of chelating agent necessary to chelate metal ions, prevent stringy texture, and produce a smooth peanut butter consistency. The exact amount of chelating agent employed is subject to such factors as the type of chelating agent employed in the mixture, the type and amount of metal ions present in the composition, the other ingredients in the composition, and the type of final product desired. The exact amount of chelating agent employed in the discontinuous aqueous phase may be varied in order to obtain the result desired in the final product and such variations are within the capabilities of those skilled in the art without the need for undue experimentation. In a preferred embodiment, the chelating agent in the discontinuous aqueous phase will be present in an amount from about 0.01% to about 5%, preferably from about 0.02% to about 3.2%, and more preferably from about 0.03% to about 1.5%, by weight of the discontinuous aqueous phase.

In yet another embodiment, additional, non-coagulable protein may also be added to the aqueous phase to fortify or enhance the protein content of the peanut butter. Examples of additional, non-coagulable protein include protein from grain and vegetable sources such as peanut flour, oat flour, soy flour, wheat flour, and corn flour. Preferably, a protein complexing agent is added to the aqueous protein phase prior to, or simultaneously with, addition of the additional non-coagulable protein to bind the additional protein, reduce the hygroscopicity of the protein, and enhance mixing of the phases. When additional non-coagulable protein is added to the aqueous protein phase without a protein complexing agent, the additional non-coagulable protein tends to absorb water from the aqueous phase resulting in a dry, thick, sticky composition. Examples of protein complexing agents and the amounts to be employed have been set out above. In a preferred embodiment, the additional, non-coagulable protein will be present in the discontinuous coagulated protein aqueous phase in an amount from about 1% to about 30%, preferably from about 1% to about 15%, and more preferably from about 1% to about 8%, by weight of the discontinuous coagulated protein aqueous phase.

The amount of discontinuous coagulated protein aqueous phase present in the continuous peanut butter oil phase of the present invention is an effective amount. An effective amount of discontinuous coagulated protein aqueous phase is a sufficient amount of discontinuous coagulated protein aqueous phase to reduce the fat or oil content of the peanut butter composition to a significant value without inverting the water-in-oil emulsion into an oil-in-water emulsion. The exact amount of discontinuous coagulated protein aqueous phase employed is subject to such factors as the type of discontinuous coagulated protein aqueous phase employed in the mixture, the type of peanut butter oil phase, the other ingredients in the composition, and the type of final product desired. The exact amount of discontinuous coagulated protein aqueous phase employed in the continuous peanut butter oil phase may be varied in order to obtain the result desired in the final product and such variations are within the capabilities of those skilled in the art without the need for undue experimentation. In a preferred embodiment, the discontinuous coagulated protein aqueous phase in the reduced-fat peanut butter composition will be present in an amount from about 10% to about 90%, preferably from about 10% to about 80%, and more preferably from about 10% to about 60%, by weight of the reduced-fat peanut butter composition.

The present invention extends to methods for making the reduced-fat peanut butter compositions. The peanut butter components are admixed using standard techniques and apparatus known to those skilled in the art. In a typical method, the reduced-fat peanut butter compositions of the present invention are prepared by admixing the continuous peanut butter oil phase and an effective amount of the discontinuous coagulated protein aqueous phase. Other ingredients will usually be incorporated into the composition as dictated by the nature of the desired composition as well known by those having ordinary skill in the art. The ultimate peanut butter compositions are readily prepared using methods generally known in the food technology and confectionery arts.

In a preferred embodiment, the components of the continuous peanut butter oil phase and the discontinuous coagulated protein aqueous phase are first premixed before admixing the phases. Premixing the components of the continuous peanut butter oil phase forms a reduced-hygroscopic peanut butter protein composition which retains a smooth consistency and is more easily blended with the aqueous phase. Premixing the components of the discontinuous coagulated protein aqueous phase forms a more intimate mixture of components which reacts more efficiently in the enzymatic protein coagulation reaction. For example, an aqueous solution of protein complexing agent can be premixed with the peanut butter to form the oil phase. The protein coagulating agent or enzyme can be dissolved in an aqueous solution of a coagulable protein at a temperature of about 38° C. to about 50° C. over a period of about 2 to 10 minutes to form the aqueous phase. The optimal temperatures utilized may vary depending upon the type of coagulable protein and the protein coagulating agent or enzyme but such temperatures are readily determined by those skilled in the art without undue experimentation. Once the continuous peanut butter oil phase and the discontinuous coagulated protein aqueous phase are premixed, the aqueous phase is then dispersed throughout the continuous peanut butter oil phase by generating enough shear force with such mixing equipment as a Stephen Cutter, Waring Blender, Bowl Chopper, and the like, to form globules of about 50 microns or less to emulsify the aqueous phase in the oil phase. This emulsification step should preferably take place in a temperature controlled state so that the stabilizing agent does not liquify and cause the phases to separate. The protein coagulating enzyme generally reacts with the coagulable protein over a period of about 20 minutes to about 1 hour depending upon the temperature of the water-in-oil emulsion, generally from about 20° C. to about 50° C. to coagulate the protein and stabilize the aqueous phase so that the aqueous phase remains in the oil phase as discrete small particles. Additional non-coagulable protein may then be admixed with the aqueous protein phase along with additional protein complexing agent to fortify the protein content of the peanut butter. Polydextrose may then be admixed with the aqueous protein phase as a plasticizing agent to promote the fluidity of the emulsion.

The peanut butter compositions may be prepared using standard techniques and equipment known to those skilled in the art. The apparatus useful in accordance with the present invention comprises mixing and heating apparatus well known in the food and confectionery manufacturing arts, and therefore the selection of the specific apparatus will be apparent to the artisan.

In a specific embodiment, the present invention is directed to a method for preparing a reduced-fat peanut butter composition in the form of a water-in-oil emulsion which comprises the steps of:

(1) providing the following ingredients:
  (a) peanut butter;
  (b) an aqueous solution comprising an effective amount of a protein complexing agent to reduce the hygroscopic properties of the peanut butter;
  (c) an aqueous solution comprising a coagulable protein selected from the group of dairy and vegetable proteins consisting of milk protein, egg protein, soy bean protein, and peanut protein; and
  (d) a protein coagulating agent;

(2) premixing the peanut butter and the aqueous solution of protein complexing agent to form a peanut butter oil phase;

(3) admixing the aqueous solution of coagulable protein and the protein coagulating agent to form an coagulated protein aqueous phase; and (4) admixing the peanut butter oil phase and the aqueous protein phase to form a reduced-fat peanut butter composition having a continuous peanut butter oil phase and a discontinuous coagulated protein aqueous phase.

In another embodiment, the aqueous protein phase of the reduced-fat peanut butter composition further comprises sufficient water-soluble solids to yield a water activity in the range from about 0.6 to about 0.9 and a water-soluble solids value from about 55% to about 82%, by weight of the discontinuous coagulated protein aqueous phase. In yet another embodiment, the aqueous protein phase of the reduced-fat peanut butter composition further comprises a mixture of additional non-coagulable protein and a protein complexing agent to fortify the protein content of the peanut butter. In yet another embodiment, the aqueous protein phase of the reduced-fat peanut butter composition further comprises polydextrose as a plasticizing agent to promote the fluidity of the emulsion.

In another specific embodiment, the present invention is directed to a reduced-fat peanut butter composition in the form of a water-in-oil emulsion prepared by a method which comprises the steps of:

(1) providing the following ingredients:
  (a) peanut butter;
  (b) an aqueous solution comprising an effective amount of a protein complexing agent to reduce the hygroscopic properties of the peanut butter;
  (c) an aqueous solution comprising a coagulable protein selected from the group of dairy and vegetable proteins consisting of milk protein, egg protein, soy bean protein, and peanut protein; and
  (d) a protein coagulating agent;

(2) premixing the peanut butter and the aqueous solution of protein complexing agent to form a peanut butter oil phase;

(3) admixing the aqueous solution of coagulable protein and the protein coagulating agent to form an coagulated protein aqueous phase; and (4) admixing the peanut butter oil phase and the aqueous protein phase to form a reduced-fat peanut butter composition having a continuous peanut butter oil phase and a discontinuous coagulated protein aqueous phase.

The reduced-fat peanut butter compositions of the present invention have improved taste and texture properties over conventional reduced-fat peanut butter compositions and fewer calories than conventional peanut butter compositions.

Once prepared, the reduced-fat peanut butter compositions may be used directly, may be stored for future use, or may be formulated in effective amounts with conventional edible carriers, in place of regular peanut butter, to prepare a wide variety of edible compositions such as cookies, candies, sauces, and the like. The reduced-fat peanut butter compositions of the present invention can be incorporated into edible carriers by admixing the inventive peanut butter composition into conventional confections. A variety of traditional ingredients known to one having ordinary skill in the food and confectionery art may be optionally included in effective amounts in the edible composition. Examples of edible carriers and the preparation of edible and confectionery formulations is set out above.

The amount of the inventive reduced-fat peanut butter composition employed in an edible composition is an effective amount to provide satisfactory flavor and nutritional value to the edible composition. The exact amount of the reduced-fat peanut butter composition employed is a matter of preference, subject to such factors as the type of edible carrier employed in the composition, the type of reduced-fat peanut butter composition employed, and the other ingredients in the composition. Thus, the amount of reduced-fat peanut butter composition may be varied in order to obtain the result desired in the final product and such variations are within the capabilities of those skilled in the art without the need for undue experimentation. In general, the amount of reduced-fat, peanut butter composition normally present in an edible composition will be up to about 90%, preferably from about 20% to about 85%, and more preferably from about 25% to about 80%, by weight of the edible composition.

The present invention extends to methods for making the edible compositions. In such a method, a composition is made by admixing an effective amount of the reduced-fat peanut butter composition of the present invention with an edible carrier and the other ingredients of the final desired edible composition. The reduced-fat peanut butter composition may be admixed with the edible carrier in any conventional manner such as by preparing a homogeneous mixture of the components, forming a peanut butter core coated by an edible carrier such as chocolate, or coating a confectionery carrier with the peanut butter composition. Other ingredients will usually be incorporated into the composition as dictated by the nature of the desired composition as well known by those having ordinary skill in the art. The ultimate edible compositions are readily prepared using methods and apparatus generally known in the food technology arts.

In another embodiment, the present invention is directed at a method for retarding fat or oil migration in a peanut butter containing chocolate confection such as a chocolate confection center-filled with peanut butter. Fat or oil migration in a chocolate confection, commonly known as "bloom", is the tendency for polyunsaturated fatty acids, such as those found in peanut butter, to migrate into the chocolate portion of a confectionery. The polyunsaturated fatty acids carry the monounsaturated fatty acids found in the chocolate portion to the surface of the confection where the monounsaturated fatty acids crystallize or "bloom". Applicants have found that when hygroscopic proteins such as those in peanut butter are treated with a protein complexing agent to reduce the hygroscopic properties of the protein, the tendency for the polyunsaturated fatty acids in the peanut butter to migrate into the chocolate portion of a confection is also reduced.

In a preferred embodiment, the present invention is directed to a method for retarding oil and fat migration in a chocolate confection which contains peanut butter which comprises the steps of:

(1) forming a homogeneous premixture of
   (a) peanut butter, and
   (b) an effective amount of a protein complexing agent to retard fat or oil migration in the peanut butter; and
(2) incorporating the peanut butter premixture from step (1) into the chocolate confection.

Throughout this application, various publications have been referenced. The disclosures in these publications are incorporated herein by reference in order to more fully describe the state of the art.

The present invention is further illustrated by the following examples which are not intended to limit the effective scope of the claims. All parts and percentages in the examples and throughout the specification and claims are by weight of the final composition unless otherwise specified.

EXAMPLES 1–2

These examples demonstrate the preparation of peanut butter compositions employing a discontinuous aqueous gelatin phase.

The aqueous gelatin compositions employed in the peanut butter compositions of Examples 1 and 2 had the compositions set out below.

| | Aqueous Gelatin Compositions | |
|---|---|---|
| | Examples | |
| Ingredients | 1 | 2 |
| Water | 50% | 51.5% |
| Sucrose | 47% | 47% |
| Gelatin | 3% | 1.5% |

The aqueous gelatin compositions of Examples 1 and 2 were admixed and heated to the boiling point of the compositions. The gelatin solutions were then cooled to about 44° C. and admixed with an equivalent amount by weight of peanut butter (Skippy) in a Waring Blender.

The peanut butter mixture of Example 1 quickly became viscous and difficult to blend. The heat generated during the shearing necessary to blend the mixture caused the peanut butter oil to separate. Oil separation was also observed in the peanut butter mixture of Example 2. After refrigeration, the peanut butter mixture of Example 2 was also judged unacceptable because the mixture had a jello-like texture.

EXAMPLE 3

This example demonstrates the preparation of a peanut butter composition employing a discontinuous aqueous light pancake syrup phase.

Light pancake syrup (Log Cabin) and peanut butter were admixed in equal amounts by weight in a Waring Blender. The peanut butter mixture was easy to blend well initially but soon became very viscous. The heat generated during the shearing necessary to blend the mixture caused the peanut butter oil to separate. Cooling the peanut butter, the light pancake syrup, or both before admixing the components did not prevent phase separation.

EXAMPLE 4

This example demonstrates the preparation of a reduced-fat peanut butter composition comprising a discontinuous coagulated protein aqueous phase, which is immobilized after being admixed into peanut butter, in accord with present invention.

The aqueous protein composition employed in the peanut butter composition of Example 4 had the composition set out below.

| Aqueous Protein Composition | |
|---|---|
| Ingredients | Example 4 |
| 1% Fat Milk | 16 oz |
| Aqueous Rennet solution (5%) | 10 g |
| Calcium Gluconate | 4 g |
| Sucrose | 34 g |
| Gelatin | 4 g |
| Aqueous Vanilla Solution (1%) | 3.5 g |

The components of the aqueous protein composition, except for the aqueous rennet solution, were admixed and heated to about 50° C. The aqueous rennet solution was then added to the protein mixture and the entire mixture was admixed with an equivalent amount by weight of peanut butter in a Waring Blender.

The peanut butter mixture of Example 4 was initially quite fluid and easy to blend. After about 20 to 25 seconds of being mixed, the peanut butter mixture began to thicken and smooth and finally set within a period of about 2 to about 4 minutes. The resulting peanut butter product had very good peanut butter taste, texture, color, and spreadability.

EXAMPLES 5–6

These examples demonstrate the preparation of peanut butter compositions employing a discontinuous soluble solids aqueous phase with and without a calcium compound.

The aqueous soluble solids compositions employed in the peanut butter compositions of Examples 5 and 6 had the compositions set out below.

| Soluble Solids Aqueous Compositions | | |
|---|---|---|
| | Examples | |
| Ingredients | 5 | 6 |
| Light Pancake Syrup | 50% | 49.05% |
| Sucrose solution (60%) | 50% | 49.05% |
| Calcium Gluconate | — | 1.9% |

The aqueous soluble solids compositions of Examples 5 and 6 were admixed and heated to the boiling point of the compositions. The solutions were then cooled to about 44° C. and admixed with an equivalent amount by weight of peanut butter in a Waring Blender.

The peanut butter mixture of Example 5 soon became dry and stiff. The heat generated during the shearing necessary to blend the mixture caused the peanut butter to separate. The peanut butter mixture of Example 6 did not become dry and was easy to mix.

These Examples demonstrate that the protein in the peanut butter oil phase tends to absorb water from the aqueous high soluble solids phase causing the resulting two-phase mixture to become dry and difficult to mix. When a calcium compound is present in the aqueous phase, the peanut protein appears to complex with the calcium resulting in a decrease in hygroscopicity. This reduced hygroscopicity results in less absorption of water by the peanut protein and smoother mixing of the oil and water phases.

EXAMPLES 7–8

These examples demonstrate the preparation of reduced-fat peanut butter compositions employing a discontinuous soluble solids aqueous phase with and without a chelating agent.

The aqueous soluble solids compositions with and without the chelating agent sodium hexametaphosphate employed in the peanut butter compositions of Examples 7 and 8 had the compositions set out below.

| Soluble Solids Aqueous Compositions | | |
|---|---|---|
| | Examples | |
| Ingredients | 7 | 8 |
| Light Corn Syrup | 49.6% | 50% |
| Aqueous Protein Phase from Example 4 | 49.6% | 50% |
| Sodium hexameta-Phosphate | 0.05% | — |
| Salt | 0.03% | — |

The aqueous soluble solids compositions of Examples 7 and 8 were admixed and heated to the boiling point of the compositions. The solutions were then cooled to about 44° C. and admixed with an equivalent amount of peanut butter by weight peanut butter in a Waring Blender.

The peanut butter mixture of Example 8 had a stringy type texture. The peanut butter mixture of Example 7 had very good texture and spreadability. These Examples demonstrate that when a chelating agent is added to the aqueous high soluble solids phase, the chelating agent tends to reduce the body of the aqueous composition and prevent the formation of a stringy texture.

EXAMPLES 9–12

These examples demonstrate the preparation of shelf-stable reduced-fat peanut butter compositions employing a discontinuous coagulated protein aqueous phase in accord with present invention.

The shelf-stable reduced-fat peanut butter compositions of Examples 9–12 were prepared by reducing the water activity and the pH value of the compositions to levels sufficient to render the products shelf stable. The compositions of the shelf-stable peanut butters of Examples 9–12 are set out below.

| Reduced-Fat Peanut Butter Compositions | | | | |
|---|---|---|---|---|
| | Examples | | | |
| Ingredients | 9 | 10 | 11 | 12 |
| Peanut butter | 40% | 50% | 50% | 50% |
| Aqueous Protein Phase from Example 4 | 20% | 12.5% | 12.5% | 12.5% |
| Light Corn Syrup from Example 7 | 20% | 30% | 30% | 30% |
| Low DE maltodextrin | 20% | 7.5% | 7.5% | 7.5% |
| Water Activity | 0.89 | 0.82 | 0.82 | 0.82 |
| pH | 5.9 | 5.9 | 5.7 | 5.72 |

The peanut butter composition of Example 9 had a water activity of 0.89 and a pH value of 5.9 which were considered not sufficiently low for shelf stability. The peanut butter composition of Example 10 had a water activity of 0.82 and a pH value of 5.9 which were considered satisfactory values for shelf stability. The peanut butter composition of Example 10 had a strong peanut butter taste, was fortified with calcium, and had half the fat of normal peanut butter. The peanut butter composition of Example 11, which was the same composition as that in Example 10 except that the pH value of the light corn syrup was lowered, had a slightly acidic tangy taste. The peanut butter composition of Example 12, which was the same composition as that in Example 10 except that the pH value of the light corn syrup was lowered, had very little tangy taste and was considered as having satisfactory shelf stability.

EXAMPLES 13–14

These examples demonstrate the preparation of peanut butter compositions containing additional, non-coagulable protein in the aqueous phase to fortify and enhance the protein content of the peanut butter. In one example, the peanut butter composition is premixed with a protein complexing agent prior to adding the non-coagulable protein and, in another example, the peanut butter composition is not premixed with a protein complexing agent prior to adding the non-coagulable protein.

Reduced-hygroscopic peanut butter protein compositions according to the present invention (Examples 13 and 14, premixed with calcium gluconate) were prepared having the compositions set out below.

| Peanut Butter Compositions | | |
|---|---|---|
| Ingredients | Examples | |
| (control) | 13 | 14 |
| Peanut butter | 266 g | 266 g |
| Calcium Gluconate (8% solution) | 40 ml | 40 ml |

The preblended peanut butter mixtures (Examples 13 and 14, with calcium gluconate) were then separately mixed with the aqueous protein compositions containing milk proteins and corn syrup set out below. The peanut butter compositions were first mixed with the milk and rennet solution to form an emulsion containing coagulated protein. This coagulated protein emulsion was then blended with the corn syrup to improve the shelf stability of the peanut butter composition. The peanut butter compositions of Examples 13 and 14 mixed smoothly, thickened rapidly, set up quickly, and had a consistency similar to that of conventional peanut butter.

| Aqueous Protein Compositions | | |
|---|---|---|
| Ingredients | Examples | |
| (control) | 13 | 14 |
| Milk proteins | 108.3 g | 108.3 g |
| 2% Rennet solution | 2.1 g | 2.1 g |
| Treated corn syrup | 173.6 g | 173.6 g |
| Peanut flour | 36.4 g | 36.4 |
| Calcium Gluconate (8% solution) | 18 ml | — |
| Polydextrose | 28.5 g | — |

The preblended peanut butter mixtures of Examples 13 and 14 were then mixed with the additional non-coagulable peanut flour protein. In the peanut butter composition of Example 13, the aqueous solution of calcium gluconate was first mixed with 636 g of the peanut butter composition in a Waring Blender; then the peanut flour was admixed into the solution to enhance the protein content of the peanut butter. Polydextrose was then admixed as a plasticizer to add creaminess to the emulsion. In the control peanut butter composition of Example 14, the peanut flour was admixed into the peanut butter without addition of calcium gluconate. The inventive peanut butter composition of Example 13 mixed smoothly, thickened rapidly, and had a consistency similar to that of conventional peanut butter. The control peanut butter composition of Example 14 became sticky and stiffened.

These Examples demonstrate that protein compositions premixed with a protein complexing agent have reduced-hygroscopic properties, retain a smooth consistency when treated with water, do not become thick and stiff, and are easier to handle. The reduced hygroscopicity results in less absorption of water by the peanut protein and smoother mixing of the oil and water phases.

EXAMPLES 15–16

These examples demonstrate the preparation of a pasta composition premixed with a protein complexing agent and a pasta composition without a protein complexing agent.

An aqueous solution of calcium gluconate (10 g of 8% solution, 0.8 g of calcium gluconate) was gently mixed with 144 g of semolina and 46.8 g of water in a Hamilton beater mixer (Example 15). A control sample of 144 g of semolina and 56 g of water was also gently mixed in a Hamilton beater mixer (Example 16).

The control pasta composition of Example 16 had a normal appearance, contained some granular lumps, held together after several squeezes but fell apart easily, and formed a sheet with a rolling pin with some difficulty. The inventive pasta composition of Example 15 had a wetter and softer appearance than the control sample, held together after several squeezes, and formed a sheet with a rolling pin very easily. After the pasta compositions of Examples 15 and 16 were cooked, the inventive pasta composition of Example 15 was softer in texture than the control pasta composition of Example 16.

The embodiments of the present invention described herein are merely exemplary and are not intended to limit the scope of the invention. Many variations and modifications may be made without departing from the spirit and scope of the invention. Applicants intend that all such modifications and variations are to be included within the scope of the invention as defined in the appended claims and their equivalents.

We claim:

1. A protein composition having reduced-hygroscopic properties which comprises a homogeneous premixture of (a) a hygroscopic protein and (b) an effective amount of a protein complexing agent to reduce the hygroscopic properties of the protein.

2. The protein composition according to claim 1, wherein the hygroscopic protein is selected from the group consisting of milk protein, egg protein, soy bean protein, wheat protein, corn protein, rice protein, oat protein, peanut protein, and leguminous protein.

3. The protein composition according to claim 1, wherein the protein complexing agent is selected from the group consisting of non-toxic water-soluble calcium compounds and magnesium compounds.

4. The protein composition according to claim 1, wherein the protein complexing agent is present in an amount from about 0.1% to about 13%, by weight.

5. An edible composition comprising an edible carrier and an effective amount of a protein composition having reduced-hygroscopic properties, wherein the protein composition comprises a homogeneous premixture of (a) a hygroscopic protein and (b) an effective amount of a protein complexing agent to reduce the hygroscopic properties of the protein.

6. The edible composition according to claim 5, wherein the edible carrier comprises sufficient water-soluble solids to yield a water activity in the range from about 0.6 to about 0.9 and a water-soluble solids value from about 55% to about 82% by weight.

7. The edible composition according to claim 5, wherein the edible carrier is chocolate.

8. A reduced-fat peanut butter composition in the form of a water-in-oil emulsion which comprises:
   (A) a premixed continuous peanut butter oil phase which comprises:
      (a) peanut butter; and
      (b) an effective amount of a protein complexing agent to reduce the hygroscopic properties of the peanut butter composition; and
   (B) a discontinuous coagulated protein aqueous phase to reduce the fat content of the peanut butter composition present in an amount from about 10% to about 90%, by weight, which comprises:
- (a) a coagulable protein selected from the group of dairy and vegetable proteins consisting of milk protein, egg protein, soy bean protein, and peanut protein present in the discontinuous coagulated protein aqueous phase in an amount from about 1% to about 30%, by weight; and
- (b) a protein coagulating agent.

9. The peanut butter composition according to claim 8, wherein the protein complexing agent is selected from the group consisting of non-toxic water-soluble calcium compounds and magnesium compounds.

10. The peanut butter composition according to claim 8, wherein the coagulable protein is milk protein.

11. The peanut butter composition according to claim 8, wherein the protein coagulating agent is a protein coagulating enzyme selected from the group consisting of rennin, *Mucor miehei, Mucor pusillus, Endothia parasitica, porcine pepsin,* and mixtures thereof.

12. The peanut butter composition according to claim 8, wherein the protein complexing agent is present in the continuous peanut butter oil phase in an amount from about 0 1% to about 13%, by weight of the continuous peanut butter oil.

13. The peanut butter composition according to claim 8, wherein the protein coagulating enzyme is present in the discontinuous coagulated protein aqueous phase in an amount from about 0.01% to about 1.2%, by weight of the discontinuous coagulated protein aqueous phase.

14. The peanut butter composition according to claim 8, wherein the discontinuous coagulated protein aqueous phase further comprises sufficient water-soluble solids to yield a water activity in the range from about 0.6 to about 0.9 and a water-soluble solids value from about 55% to about 82%, by weight of the discontinuous coagulated protein aqueous phase.

15. The peanut butter composition according to claim 8, wherein the discontinuous coagulated protein aqueous phase further comprises a chelating agent present in an amount from about 0.01% to about 5%, by weight of the discontinuous coagulated protein aqueous phase.

16. The peanut butter composition according to claim 8, wherein the discontinuous coagulated protein aqueous phase further comprises non-coagulable protein to enhance the protein content of the peanut butter composition and an effective amount of a protein complexing agent to reduce the hygroscopic properties of the non-coagulable protein.

17. The peanut butter composition according to claim 8, wherein the discontinuous coagulated protein aqueous phase further comprises polydextrose in an amount from about 1% to about 15%, by weight.

18. An edible composition which comprises an edible carrier and a reduced-fat peanut butter composition in the form of a water-in-oil emulsion, wherein the peanut butter composition comprises:
- (A) a premixed continuous peanut butter oil phase which comprises:
  - (a) peanut butter; and
  - (b) an effective amount of a protein complexing agent to reduce the hygroscopic properties of the peanut butter composition; and
- (B) a discontinuous coagulated protein aqueous phase to reduce the fat content of the peanut butter composition present in an amount from about 10% to about 90%, by weight, which comprises:
  - (a) a coagulable protein selected from the group of dairy and vegetable proteins consisting of milk protein, egg protein, soy bean protein, and peanut protein present in the discontinuous coagulated protein aqueous phase in an amount from about 1% to about 30%, by weight; and
  - (b) a protein coagulating agent.

19. A method for preparing a reduced-fat peanut butter composition in the form of a water-in-oil emulsion which comprises the steps of:
- (1) providing the following ingredients:
  - (a) peanut butter;
  - (b) an aqueous solution comprising an effective amount of a protein complexing agent to reduce hygroscopic properties of the peanut butter;
  - (c) an aqueous solution comprising a dairy or vegetable protein selected from the group consisting of milk protein, egg protein, soy bean protein, and peanut protein; and
  - (d) a protein coagulating agent;
- (2) premixing the peanut butter and the aqueous solution of protein complexing agent to form a peanut butter oil phase;
- (3) admixing the aqueous solution of coagulable protein and the protein coagulating agent to form an coagulated protein aqueous phase; and
- (4) admixing the peanut butter oil phase and the aqueous protein phase to form a reduced-fat peanut butter composition having a continuous peanut butter oil phase and a discontinuous coagulated protein aqueous phase.

20. A reduced-fat peanut butter composition in the form of a water-in-oil emulsion prepared by a method which comprises the steps of:
- (1) providing the following ingredients:
  - (a) peanut butter;
  - (b) an aqueous solution comprising an effective amount of a protein complexing agent to reduce the hygroscopic properties of the peanut butter;
  - (c) an aqueous solution comprising a coagulable protein selected from the group of dairy and vegetable proteins consisting of milk protein, egg protein, soy bean protein, and peanut protein; and
  - (d) a protein coagulating agent;
- (2) premixing the peanut butter and the aqueous solution of protein complexing agent to form a peanut butter oil phase;
- (3) admixing the aqueous solution of coagulable protein and the protein coagulating agent to form an coagulated protein aqueous phase; and
- (4) admixing the peanut butter oil phase and the aqueous protein phase to form a reduced-fat peanut butter composition having a continuous peanut butter oil phase and a discontinuous coagulated protein aqueous phase.

21. A method for retarding oil and fat migration in a chocolate confection containing peanut butter which comprises the steps of:
- (1) forming a homogeneous premixture of
  - (a) peanut butter, and
  - (b) an effective amount of a protein complexing agent to retard fat or oil migration in the peanut butter; and
- (2) incorporating the peanut butter premixture from step (1) into the chocolate confection.

* * * * *